US009339566B2

(12) United States Patent
Smith et al.

(10) Patent No.: US 9,339,566 B2
(45) Date of Patent: May 17, 2016

(54) HIGH VELOCITY HOT AIR STERILIZATION SYSTEM EMPLOYING THE INSTRUMENT CONTAINER AS STERILIZATION CHAMBER

(71) Applicant: Integrated Medical Technologies, Inc., Bloomington, IL (US)

(72) Inventors: William Bryan Smith, Bloomington, IL (US); Nelson Sigman Slavik, Niles, MI (US); John Howland Hinman, Honeoye Falls, NY (US); Jeffrey S. Crane, Geneseo, NY (US)

(73) Assignee: Integrated Medical Technologies, Inc., Bloomington, IL (US)

( * ) Notice: Subject to any disclaimer, the term of this patent is extended or adjusted under 35 U.S.C. 154(b) by 286 days.

(21) Appl. No.: 14/170,752

(22) Filed: Feb. 3, 2014

(65) Prior Publication Data

US 2015/0217007 A1  Aug. 6, 2015

Related U.S. Application Data

(60) Provisional application No. 61/760,045, filed on Feb. 2, 2013.

(51) Int. Cl.
*A61L 2/06* (2006.01)

(52) U.S. Cl.
CPC ........................ *A61L 2/06* (2013.01)

(58) Field of Classification Search
CPC .................................... A61L 2/06; A61L 2/26
See application file for complete search history.

(56) References Cited

U.S. PATENT DOCUMENTS

2008/0240981 A1* 10/2008 Berentsveig ........... A01N 25/06
422/29

* cited by examiner

*Primary Examiner* — Regina M Yoo
(74) *Attorney, Agent, or Firm* — Singleton Law Firm, P.C.

(57) ABSTRACT

A device and system is disclosed for sterilizing objects, commonly dental, medical, or veterinary instruments, by directing high velocity hot air into a container having pre-constructed plenums to direct, diffuse, and re-circulate the sterilizing agent uniformly throughout the chamber to effect sterilization of contained medical objects. More specifically, the invention employs high velocity hot dry air as the sterilizing agent, generating the heat and rapid airflow by means of a base unit. The high velocity heated air is forced into the medical instrument container where a removable air supply/return plenum directs the heated, rapidly flowing air uniformly throughout the container. During the sterilization process heated air temperature is maintained in the container by a continual re-circulating of exhaust air back to the base unit for re-heating and return to the container. Upon completion of the sterilization process the container is removed from the base unit, sealing air supply and exhaust air container portals to assure continued sterility of the contained instruments within the container.

6 Claims, 14 Drawing Sheets

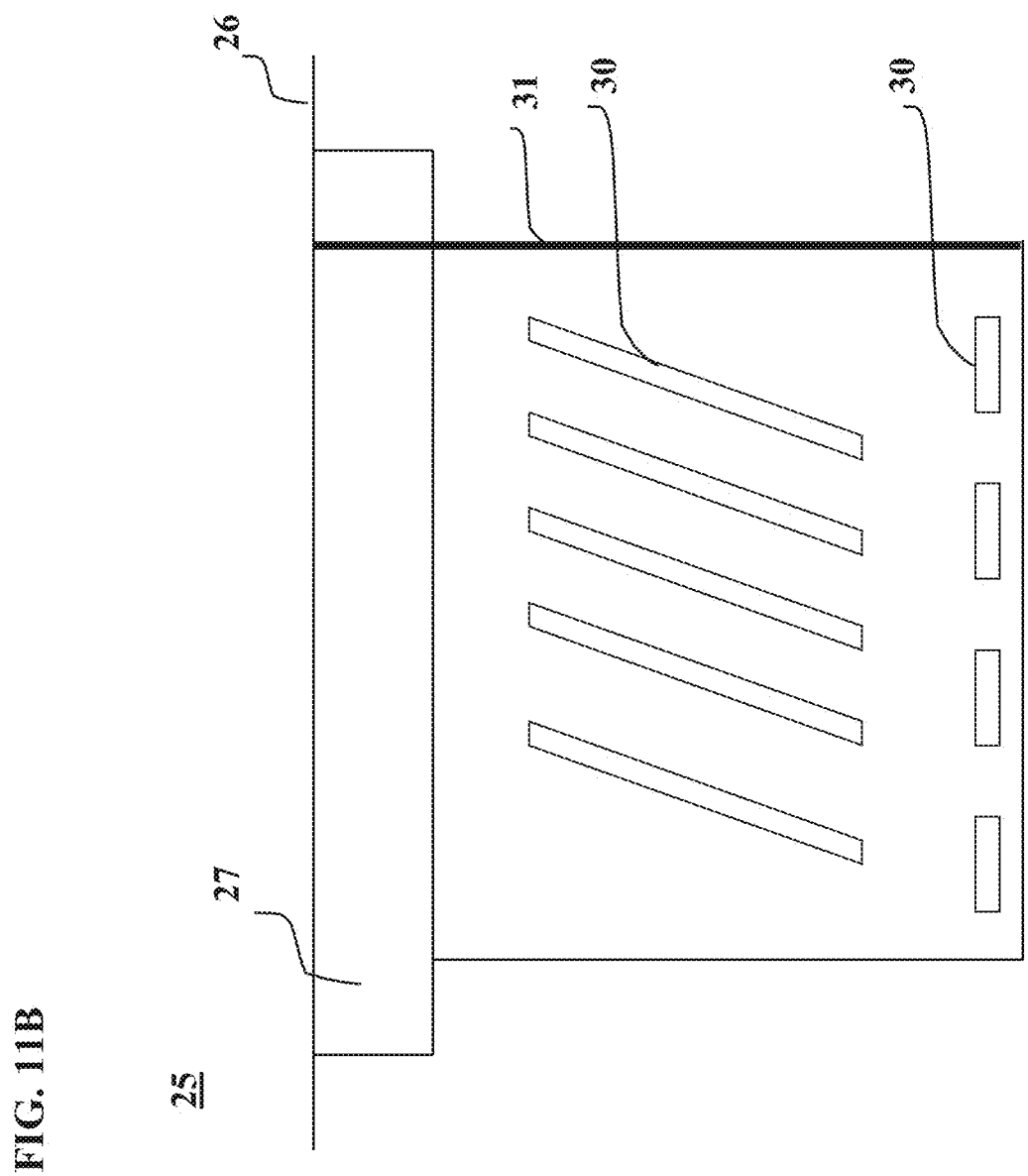

HIGH VELOCITY HOT AIR STERILIZATION SYSTEM EMPLOYING THE INSTRUMENT CONTAINER AS STERILIZATION CHAMBER

RELATED APPLICATIONS

This application is a continuation-in-part of U.S. application Ser. No. 61/760,045, filed on Feb. 2, 2013.

BACKGROUND OF THE INVENTION

The present disclosure describes an apparatus and process for sterilization of items, most notably surgical instruments, used in medical, dental, veterinary, or other patient-care markets. The invention relates, more particularly to an improved high velocity dry heat sterilization device to prohibit the introduction of microbial contaminants to the sterilization chamber during the entire sterilization cycle and to ensure such items once sterilized, remain sterile when removed from the high velocity dry heat sterilization device.

There are three distinct types of dry heat sterilizers: (1) Static hot air sterilizers in which air convection is generated solely by gravity as hot air rises and cooler air descends; (2) Mechanical convection sterilizers in which air is moved by blowers to uniformly distribute the heated air and equally transfer heat throughout the load; and (3) High velocity hot air sterilizers in which air is moved at a high rate, such as at 2500 feet per minute, with the flowing air serving as the heat transfer medium. Both static air and mechanical convection sterilizers require minimally one hour (at 340° F.) or two hours (at 320° F.) to achieve sterilization whereas the high velocity hot air sterilizer can sterilize in six to twelve minutes (at 375° F.), depending on instrument type or packaging.

A high velocity hot air sterilization device has been disclosed by Cox et al. in U.S. Pat. Nos. 4,824,644; 4,894,207; 4,923,681; and 4,975,245. This device was designed and marketed for use in the dental and orthodontic markets to rapidly sterilize small instruments without instrument corrosion. The Cox High Velocity Hot Air Sterilization Device accommodates wrapped or unwrapped instruments which are placed into a wire mesh, open basket and held for pre-designated times at 375° F. as prescribed under the U.S. Food and Drug Administration 510(k) notification (K8726643A and K881371). Upon completion of the sterilization cycle, the basket containing the instruments is removed from the sterilizer. In this system described by Cox et al., unwrapped instruments are subjected to potential microbial contamination from environmental sources during the sterilization process and upon removal from the sterilizer since the sterilizer allows outside air to circulate within the sterilization chamber during the sterilization cycle and because the trays are subjected to outside air following removal from the sterilizer. For dental procedures this practice is acceptable since sterilization of dental instruments has placed emphasis on obtaining complete kill of microorganisms originating from previous patients with no concern regarding contamination from microbial contaminants having environmental origin. Other high velocity hot air sterilization devices by Allen and Sildve (U.S. Pat. No. 4,935,604) and Goldman (U.S. Pat. No. 6,039,926) also operate in a similar fashion that allows unwrapped instruments to be subjected to environmental microbial contaminants.

Existing high velocity hot air sterilization devices do not address the introduction of environmental microbial contaminants during the sterilization process or afterward as detrimental to dental patient care. Most orthodontic and dental procedures are topical and are performed in an oral environment already containing high microbial concentrations and contaminants of environmental origin play no role in disease transmission from instruments. All high velocity hot air sterilization devices directly allow outside air into the air handling system by means of fans, louvered vents, or unclosed or unsealed plenums before, during, and after the sterilization cycle. In these systems any instrument or device that is not wrapped, packaged, or pouched is subjected to microbial contamination from continually introduced outside air during the sterilization cycle that has not received the prescribed time and temperature requirements necessary to ensure microbial inactivation. Upon completion of the sterilization cycle, unwrapped instruments are directly subjected to potential environmental microbial contaminants upon the opening of the sterilization chamber and their removal. No unwrapped instrument protection is afforded with existing high velocity, hot air sterilization devices.

For use in critical-care environments including dental surgical, hospital surgical, ambulatory or outpatient surgical, and veterinary surgical procedures, patient contact items must be devoid of all viable microbial contaminants to avoid infection or disease transmission. No microbial contaminants can be introduced during the sterilization process, nor can they be introduced after the sterilization process. For unwrapped or directly exposed instruments, any air introduced to the sterilization chamber after the initiation of the sterilization cycle must be subjected to the identical sterilization parameters of designated time and temperature as the instruments being sterilized. This requirement precludes the introduction of any outside air to the air handling system and hence the sterilization chamber, once the sterilization cycle has been initiated; this requirement is not followed by the prior art high velocity hot air sterilizers.

High velocity, hot air sterilization technology has the potential to meet the sterilization requirements of the critical-care medical environment as a standard sterilization technology for heat-resistant instruments or devices. However, the original design of high velocity hot air sterilizers has also limited its usefulness due to the sterilizer's inability to accommodate closed instrument containers that could assure internal sterilization parameters are achieved within an instrument container for instrument sterilization and yet maintain the sterility of those instruments from environmental microbial contamination once the instrument container was removed from the sterilizer chamber.

Although wrapping instruments had been a primary mechanism of maintaining instrument sterilization using wet steam heat, static dry heat, high velocity hot air, radiation, and chemical agents in the past, emphasis has shifted to the use of closed containers for sterilizing larger quantities of instruments and providing subsequent protection from environmental microbial contaminants. With the increased use of closed container systems in critical-care medical environments, the use of closed containers in dental practices has also become the preferred way to protect and store sterilized dental instruments.

Closed containers allowing migration of the sterilizing agent into the container for instrument sterilization have been developed to accommodate specific sterilizing agents. The design of the container and/or its portal design must be congruent with the attributes of the sterilizing agent and must not interfere with the influx of the sterilizing agent. Accordingly the container design must assure the protection of the sterilized instruments from microbial agent contamination from the point of the container's removal from the sterilizer until the container is opened for instrument use within the sterile field.

Closed containers have been designed to incorporate top and bottom perforations protected by a microbial filtering material permeable to gas or vapor sterilants, but impermeable to microorganisms. These perforations may be static, remaining continuously open and filtered. An example of such a container is described in U.S. Pat. No. 4,551,311 issued Nov. 5, 1985 to Lorenz and entitled "Sterilizer Container."

Another design incorporates open side vents (U.S. Patent Application Publication No.: US 2003/0211023 A1; Su-Syin Wu and Charles Howlett; "Instrument Sterilization Container Having Improved Diffusion") to allow gas or vapor sterilants into the container. Protection from microbial contaminants is accomplished through the incorporation of internal or external microbial filters by wrapping the instruments or wrapping the entire container.

The container may also be of a non-static design, providing an automatic opening and shutting mechanism. For steam sterilization the pressure differential between the inside and outside of the container triggers an automatic opening and closing of a pressure-sensitive valve (U.S. Pat. No. 5,352,416 issued Oct. 4, 1994 to Wagner and entitled "Valve Arrangement for a Sterilization Container").

High velocity hot air sterilizers employ rapidly flowing hot air over the surface of an article to affect microbial kill Hot air influx into the container at a sufficient rate is therefore necessitated to achieve sterilization in the prescribed time-temperature profile. Any barrier to that necessitated rate of airflow will significantly impact sterilization conditions. Research has demonstrated that container perforation coupled with fabric filtration will disturb the high velocity influx of hot air into the instrument container and have significant impact on the conditions necessary to achieve reliable instrument sterilization. Sterilization conditions cannot be achieved within an instrument container employing high velocity hot air as the sterilant when using air filtration devices designed to prevent the influx of microbial contaminants. Existing instrument containers that employ perforations in the top, sides, and/or bottom of the container also require fabric filtration to mitigate microbial contaminants and thus, prohibit the necessary conditions required for instrument sterilization by high velocity hot air. Existing instrument containers that utilize pressure valves were specifically designed for pressurized wet steam sterilizers and do not function under the non-pressurized treatment conditions employed in high velocity dry heat sterilization. Static, open vent designs still require instrument or container wrapping.

A need exists in the art for a high velocity hot air sterilizer that provides and maintains sterile conditions within the high velocity hot air sterilizer's air handling system and sterilization chamber during the complete sterilization cycle. A need also exists in the art for a high velocity hot air sterilizer that provides the capability to sterilize medical instruments within an instrument container that allows re-distribution of sterile air during the sterilization cycle, yet can be closed and sealed before removal from the high velocity hot air sterilizer upon the completion of the sterilization cycle to assure instrument sterility to point of use.

U.S. patent application Ser. No. 14/073,536 (Slavik, 2013) provides a mechanism that allows rapidly flowing hot air to enter an instrument container. This mechanism incorporates a sliding door into the instrument container to be opened during the sterilization cycle and closed upon its completion. The mechanism to open and close the container's sliding door is incorporated within the sterilizer with both components being integral to one another in their operation.

The present invention provides a novel alternative to the one described by Slavik, 2013 by supplying high velocity hot air from the high velocity hot air sterilizer to the instrument container by means of an air supply portal and directing that air flow over the instruments by means of an inserted and removable plenum and directed air vents housed in the container, thus providing the airflow and temperature required of high velocity hot air sterilization. Instrument container air is continuously re-circulated from the container to the high velocity hot air sterilizer by means of a second portal, re-directing it to the base unit for re-heating for re-introduction at the designated velocity and temperature back into the instrument container. This process continues through the completion of the sterilization cycle at which time the container is removed from the high velocity hot air sterilizer. Upon the container's removal, the instrument container's air supply and exhaust ports are automatically closed, sealed, and latched to ensure that the sterilized instruments remain sterile within the instrument container.

SUMMARY OF THE INVENTION

The present disclosure describes a high velocity hot air sterilization device for sterilizing medical, dental, or veterinary instruments or other objects used in critical-care environments. The sterilization device described herein is an improvement over prior devices because the sterilization device described herein (1) incorporates a closed and sealed recirculating air handling system and sterilization chamber during the course of the sterilization cycle and (2) provides the capacity within the high velocity hot air sterilization device to sterilize instruments within an instrument container that allows the parameters necessary of high velocity hot air sterilization, yet can be closed and sealed to prevent instrument contamination once the container is removed from the sterilization device.

More specifically, the disclosure describes a sterilization device having: (1) the ability to sterilize trays or racks of instruments and objects within an instrument container or in an open basket configuration, wrapped or unwrapped and ensure such are not subject to any outside air entering the sterilization chamber and all aspects of the sterilizer's air handling system during the course of the sterilization cycle; (2) the ability to generate and supply high velocity hot air to instruments, objects, or instrument containers therein said high velocity hot air sterilizer device being configured to deliver to the sterilization chamber only high velocity hot air that undergoes the identical sterilization parameters of time and temperature prescribed by the U.S. Food and Drug Administration (FDA) for the sterilization of instruments; (3) the ability to maintain the sterilization chamber's sterilized environment by ensuring all sterilizer doors, air handling plenums, vents, and other potential air infiltration areas are sealed to prevent the flow of external air into the air handling system or sterilization chamber during the sterilization cycle; and (4) the ability to accommodate instrument containers which allow the sterilization parameters of high velocity hot air sterilization be fulfilled and yet not allow the infiltration of environmental microbial contaminants once removed from the sterilizer.

The present disclosure describes the instrument container as either being positionable within the high velocity hot air sterilization device or external to the sterilization device and mateable therewith to receive high velocity hot air from the high velocity hot air sterilization device. As described herein, the container is configured to uniformly distribute the air within the container, and exhaust the air back to the closed air handling system of the high velocity hot air sterilization device for subsequent, continuous recharging of heat and air velocity and re-distribution to the instrument container during the course of the sterilization cycle. The instrument container is configured to accept and exhaust sterilizing air during the sterilization cycle. The container is also configured to close to the influx of environmental microbial agents prior to its removal from the high velocity hot air sterilizer upon completion of the sterilization cycle to assure instrument sterility until time and place of use.

Thus, the present invention relates to a high velocity hot air sterilization device for sterilizing medical, dental, veterinary instruments, or other objects requiring total sterility of such instruments or objects by providing during the course of the sterilization cycle a closed and sealed, recirculating air handling system and sterilization chamber which disallows the influx, intrusion, or infiltration of outside contaminated air to come into contact with aforementioned instruments or objects.

The high velocity hot air sterilization device consists of an air handling system comprised of (1) a recirculating fan with associated plenum, (2) an electric heating coil or similar device (3) a hot air supply plenum, (4) a sterilization chamber, and (5) a return air plenum. The air handling system is completely sealed and closed to the infiltration of outside air once the sterilization cycle is initiated. Air contained in the air handling system is brought to the prescribed air velocity by means of the recirculating fan. The high velocity air is subsequently directed over the electric heating coil to bring that air to the prescribed temperature. The heated, high velocity air is then directed to the sterilization chamber via the hot air supply plenum where it is uniformly distributed throughout the sterilization chamber; the sterilization chamber is a space suitable for holding the instruments to be sterilized. In the preferred embodiment, the instrument container is the sterilization chamber. In another instance the sterilization chamber, containing a basket or tray which holds instruments, is integral to the sterilizer.

Air from the sterilization chamber is subsequently directed into the return air plenum which then directs the air to the recirculating fan which recycles the air through the aforementioned system. Hot, high velocity air is continuously recirculated through the air handling system during the complete sterilization cycle to maintain the air temperature and air velocity conditions required to sterilize instruments and objects. At no time during the sterilization cycle is outside air allowed to enter or infiltrate any subset of the air handling system or sterilization chamber.

Preferably, the high velocity hot air sterilizer, sterilization chamber, and all its subparts are comprised of materials able to withstand the rigors presented by the temperatures utilized in high velocity hot air sterilization (375 degrees F. or higher). Preferably, these materials include stainless steel, aluminum, high temperature resistant thermoplastic and thermosetting polymers, ceramics, silicone, and nylon fabric plastics.

Preferably, the high velocity hot air sterilizer contains the mechanism to heat the air to its required temperature, to give the heated air its required velocity, to deliver the high velocity hot air to the sterilization chamber, and to continuously re-circulate the air to maintain the prescribed air velocity and temperature required throughout the complete sterilization cycle.

Preferably, the high velocity hot air sterilizer and associated air handling system are sealed, closed and retains positive pressure relative to the outside environment to preclude the infiltration of external, non-sterile air into the sterilizer's air handling system during the sterilization cycle.

Preferably, the high velocity hot air sterilizer contains thermocouples, an air flow velocity meter, and a timer integrated with a controller to properly monitor, maintain, and record desired temperatures, airflow velocity, and sterilization cycle times, respectively, to ensure proper sterilization conditions.

Preferably, the high velocity hot air sterilizer contains pressure gauges and transmitters integrated with a controller to properly monitor and maintain positive air pressure in the air handling system to preclude the infiltration of external air in the event of inadequate positive air pressure.

The aforementioned monitoring devices are integrated with a controller. The fans and heaters described herein are also integrated with the controller. The controller is a microcontroller based system with high-resolution ADCs (analog-to-digital converter) to read the monitoring devices input data such as temperature, pressure and air flow and provide control of the output devices such as the blowers, heaters and alarms. The controller is also integrated with an input system, such as a touch screen, keyboard, or other suitable input system, to allow a user to change settings, run a sterilization cycle, or otherwise control the hot air sterilization system. In addition, the controller will also provide operating instructions and system status information for the user through a display system such as a LCD or LED display.

Preferably, the high velocity hot air sterilizer contains a cooling cavity surrounding the sterilization chamber in which its contained air remains separated and segregated from the sterilizer chamber and its associated air handling system.

Preferably, the high velocity, hot air sterilizer has a locking mechanism on the sterilizer door to maintain an airtight door seal during the sterilization process.

Preferably, the instrument container is positioned into the high velocity, hot air sterilizer by its placement onto a sliding tray, which guides the instrument container into and out of the high velocity hot air sterilizer and assures the proper alignment and positioning of the high velocity hot air sterilizer's hot air supply and exhaust portals with corresponding air supply and exhaust portals of the instrument container.

The instrument container includes moveable covers which cover the hot air supply and exhaust portals of the container prior to the container being removed from the high velocity hot air sterilizer. The moveable covers are structured such that the high velocity hot air sterilizer cannot be opened unless the movable covers are in the closed position. The high velocity hot air sterilizer has a locking mechanism to ensure the moveable covers over the instrument container are covered, sealed and latched. The moveable covers may consist of both internal covers and external covers.

The instrument container internal covers can be sealed over the instrument container's internal hot supply air and spent exhaust air portals prior to the container's removal from the high velocity, hot air sterilizer.

The instrument container external covers can be sealed over the instrument container's external hot supply air and spent exhaust air portals subsequent to the container's removal from the high velocity hot air sterilizer.

Preferably, the instrument container has internal plenums that circulate the hot air within the container and direct it for uniform distribution throughout the instrument container.

Preferably, the internal plenum within the instrument container also creates an air exhaust flow where captured spent air is pulled to the exhaust portal for return to the high velocity hot air sterilizer for re-heating and re-circulation back to the instrument container via strategically placed, spaced, and oriented vents.

Preferably, the instrument container has a plenum insert that creates a plenum that circulates the hot air supply and directs it to uniformly distribute the hot air at a high velocity over the instruments to be sterilized via strategically placed, spaced, and oriented vents in the supply plenum walls.

Preferably, the plenum insert also creates an air exhaust plenum where captured spent air is pulled to the exhaust portal for return to the base unit via strategically placed, spaced, and oriented vents in the exhaust plenum walls for re-heating and re-circulation back to the instrument container.

Preferably, the air plenum insert is removable and cleanable and is sealed in place by latching the instrument container's lid, which contains heat resistant gaskets to ensure the integrity of the created plenums.

Preferably, the instrument container's design is configured to accept multiple layers of instruments and to accept instruments that are uncovered on perforated trays or in baskets or are wrapped or pouched.

BRIEF DESCRIPTION OF THE DRAWINGS

A preferred embodiment of this invention has been chosen wherein:

FIG. 11B is a front elevation view of the instrument container's plenum insert.

DESCRIPTION OF THE PREFERRED EMBODIMENT

The present disclosure describes a device suitable for prohibiting the introduction of microbial contaminants to a sterilization chamber of a high velocity dry heat sterilization device during an entire sterilization cycle and for ensuring such items, once sterilized, remain sterile when removed from the high velocity dry heat sterilization device. The preferred and described embodiment of the present invention is described below based on the accompanying drawings.

Figure 1:
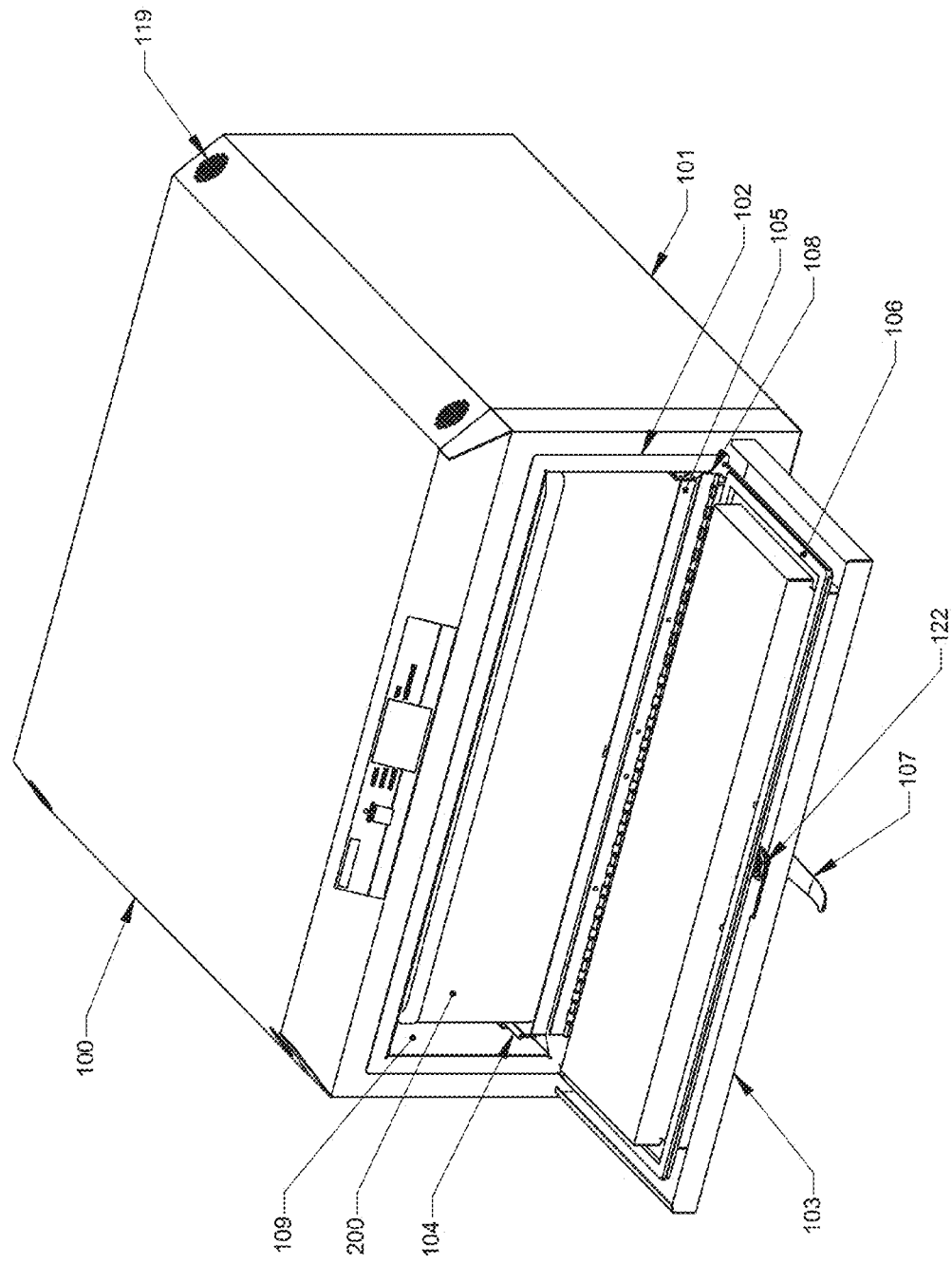
FIG. 1 is a perspective view of the recirculating high velocity hot air sterilizer with enclosed instrument container.

Referring to FIG. 1, a high velocity hot air sterilizer 100 is provided which is suitable for receiving an instrument container 200. The instrument container 200 is designed to receive, uniformly distribute, return, and recirculate high velocity hot air from the high velocity hot air sterilizer 100 to sterilize and depyrogenate wrapped and unwrapped medical and dental instruments in a containerized environment. As will be described, the high velocity hot air sterilizer 100 and the instrument container 200 have incorporated therein various structural features which provide for a closed and sealed, recirculating air handling system during the sterilization cycle that is impervious to the influx of external air and microbial contaminants during the course of the sterilization cycle and which provide the uniform circulation of high velocity hot air throughout the instrument container 200 to the held instruments and devices.

Figure 2:
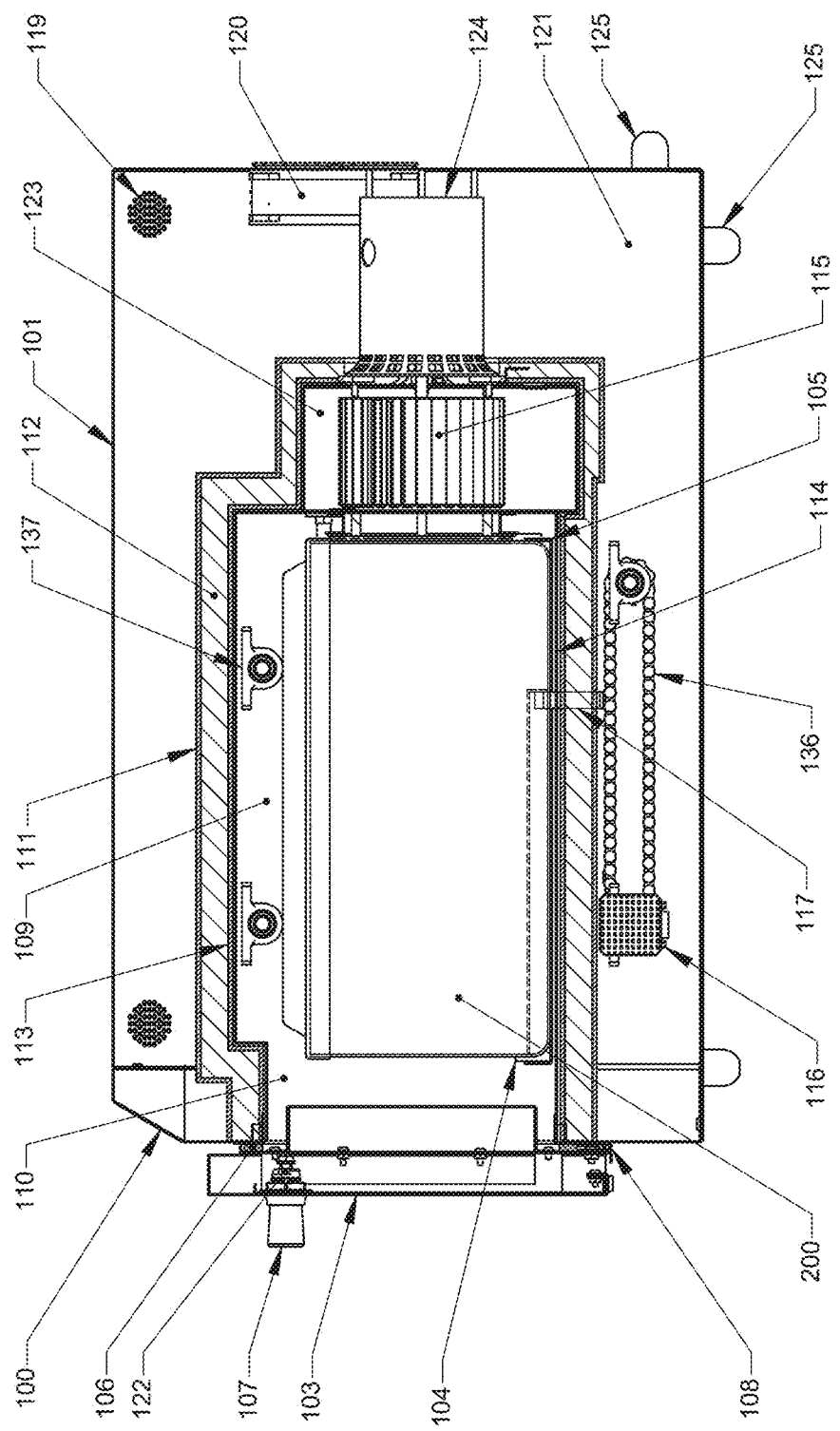
FIG. 2 is a cross-sectional side view of the recirculating high velocity hot air sterilizer, with the door in the closed position, and holding the instrument container.

Referring to FIGS. 1 and 2, the high velocity hot air sterilizer 100 includes an outer housing 101, preferably formed from metal, which surrounds a heating chamber 109. The heating chamber 109 is accessed for instrument container 200 insertion and removal via a door 103 and through a rectangular opening 110 formed in the outer housing 101. The door 103 is hingedly attached to the rectangular opening 110 and is movable between an open position and a closed position. Although it is preferred that the door 103 be hinged horizontally, a vertical hinged configuration is also envisioned. Internal to the heating chamber 109 is a sliding rack 104 which carries an instrument container tray 105. The sliding rack 104 is mounted in the heating chamber 109 and is movable between a contracted position and an extended position. The extended positioned is defined by the sliding rack 104 cantilevered over the open sterilizer door 103 for ease and proper insertion of an instrument container 200 onto the instrument container tray 105. The contracted position is defined by the sliding rack 104 and instrument container tray 105 contracted within the heating chamber 109 such that the instrument container 200 is in the proper position to align the instrument container 200 within the heating chamber 109 to begin sterilization, as is described in greater detail below. With the sliding rack 104 in the contracted position, the sterilizer door 103 is moved to the closed position and is locked into place by turning a locking door handle 107 which activates a door lock 122, thereby sealing a door gasket 106 tightly against the sterilizer door rim 102 until the completion of the sterilization cycle to prevent outside air from entering the heating chamber 109.

Figure 3:
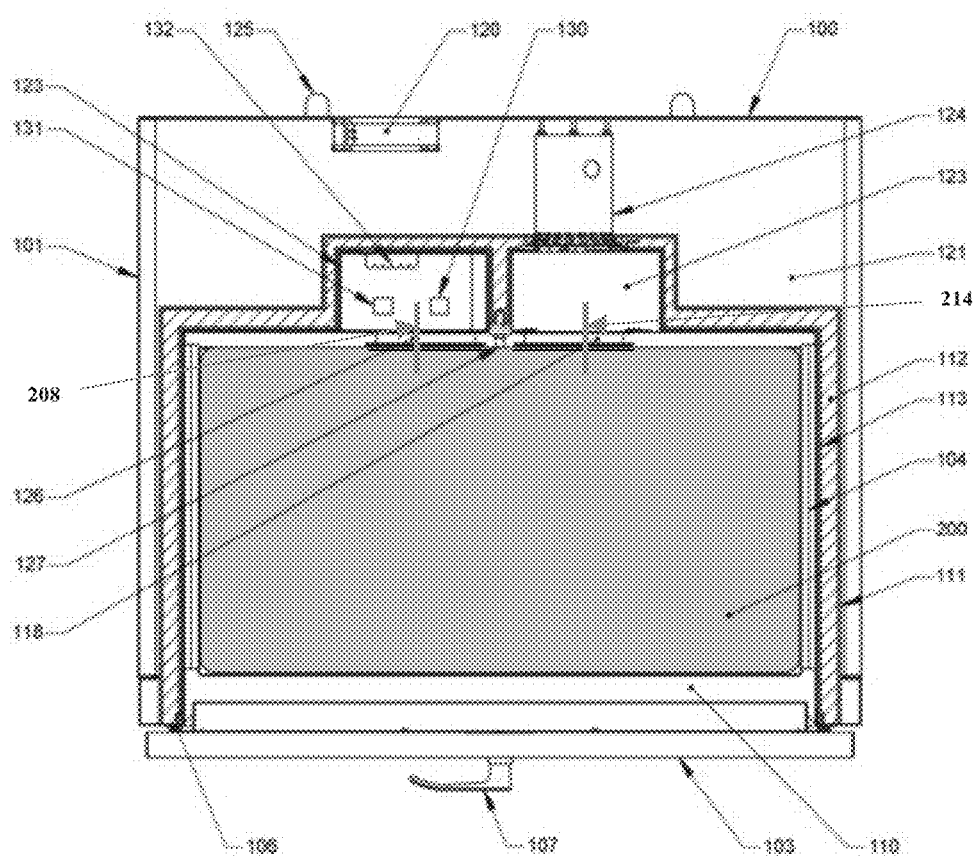
FIG. 3 is a cross-sectional top view of the recirculating high velocity hot air sterilizer, with the door in the closed position with the enclosed instrument container depicting the air handling plenum, the circulating fan, the circulating fan motor, and the cooling fan.

Referring to FIGS. 2 and 3, the heating chamber 109 is defined by a heating chamber wall 114 which defines a back, sides, top, and bottom of the heating chamber 109 and is constructed such as to preclude entry of outside air to the heating chamber 109, thereby allowing the heating chamber 109 and the associated air handling system to remain airtight when the door 103 is in the closed position during a sterilization cycle. Encompassing the exterior of the heating chamber wall 114 is an insulating jacket structure consisting of an outer insulation wall 111 and an inner insulation wall 113 with an insulating material 112 situated between the inner insulation wall 113 and outer insulation wall 111. The insulating jacket structure serves two purposes. The first purpose is to minimize heat loss from the heating chamber 109 during the sterilization cycle. The second purpose is to provide a heat barrier between the heating chamber 109 and the metal outer housing 101 of the high velocity hot air sterilizer 100.

Referring to FIG. 3, the high velocity hot air sterilizer 100 includes an air handling system which includes a circulating fan 115, an electric heating element 132, an air flow monitor 130, an air pressure monitor 131, and an air handling plenum 123. The air handling system directs and monitors supply air to the instrument container 200 and receives exhaust air from the instrument container 200. The air handling system is located adjacent the rear outside heating chamber wall 114. The air handling plenum 123 is a chamber which houses the electrical heating element 132 and the fan 115.

Referring to FIG. 3, a pair of openings is formed through the back wall of the heating chamber 109 to the air handling plenum 123. One of the openings serves as an air supply portal 126 which allows hot high velocity air to flow from the air handling system of the high velocity hot air sterilizer 100 into the instrument container 200. The other of the openings serves as an air exhaust portal 118 which allows air to exhaust from the instrument container 200 to the air handling system of the high velocity hot air sterilizer 100 where the air is re-heated and brought back to velocity before recirculation back to the instrument container 200. The air handling plenum 123 is air-tight and does not allow air infiltration or exfiltration except through the air supply portal 126 and the air exhaust portal 118. Together, the air supply portal 126 and the air exhaust portal 118 serves as an air handling portal which allows air to enter and leave the air handling plenum 123; in the preferred embodiment, the air handling portal includes a pair of opening, though a single opening is envisioned.

Referring to FIG. 3, an insulation barrier surrounds the heating chamber wall 114 and includes an outer insulation wall 111 and an inner insulation wall 113 between which is enclosed insulating material 112. As shown in FIGS. 2 and 3, the insulation barrier forms a five-sided barrier within the hot air sterilizer 100 and serves to insulate the contents of the heating chamber wall 114. The sixth side of the insulation barrier defines an opening through which the instrument container 200 is insertable within the insulation barrier. The locking door 103, when in the closed position, and the heating chamber wall 114 together define the heating chamber 109. The locking door 103, when in the closed position, forms a sealed interface with the heating chamber wall 114 to prevent air from entering the heating chamber 109.

The air handling system is positioned at the rear of the heating chamber 109 and within the heating chamber wall 114. The air handling system is primarily defined by the air handling plenum 123 which defines a pair of adjacent chambers at the rear of the heating chamber 109, as best illustrated in FIG. 3. The first chamber of the air handling plenum 123 includes the circulating fan 115 which is driven by the circulating motor 124. As shown in FIG. 3, the circulating motor is positioned outside of the heating chamber 109. The circulating motor is joined to the fan 115 by a drive element, such as a shaft, which passes through the heating chamber 109 wall 114 and the insulation barrier, but is sealed to prevent air transfer to the heating chamber 109. The second chamber of the air handling plenum 123 contains the heating element 132, the air flow monitor 130 and the air pressure monitor 131. The systems within the second chamber of the air handling plenum 123 are discussed in greater detail herein. The first chamber and the second chamber include an opening therebetween for freely communicating air between the first chamber and the second chamber.

A cooling cavity 121, as shown in FIGS. 2 and 3, is formed within the hot air sterilizer 100 and surrounds at least the rear, top and bottom of the heating chamber 109. The cooling cavity 121 serves to insulate the metal outer housing 101 from escaped heat emanating from the heating chamber 109 or air handling plenum 123 and uses outside air recirculating through the cooling cavity by aid of a cooling fan 120 which draws outside air into the cooling cavity 121 where it is subsequently vented by the aid of passive cooling vents 119 at the sides of the high velocity hot air sterilizer 100. All air within the cooling cavity 121 remains segregated from the heating chamber 109.

Rubber feet/spacers 125 are located on both the exterior back and exterior bottom of the metal outer housing 101 and serve to provide ventilation space between the high velocity hot air sterilizer 100 and the wall or tabletop or other object which the high velocity hot air sterilizer 100 is positioned near during use.

Figure 4A:
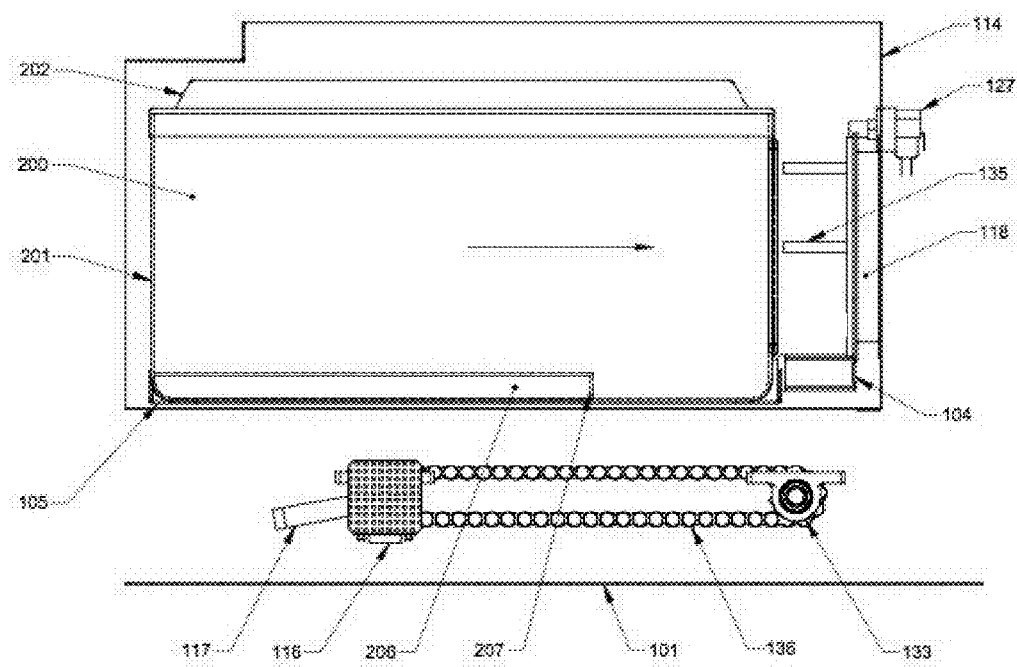
FIG. 4A is a cross-sectional side view depicting the instrument container partially inserted into the heating chamber.
Figure 4B:
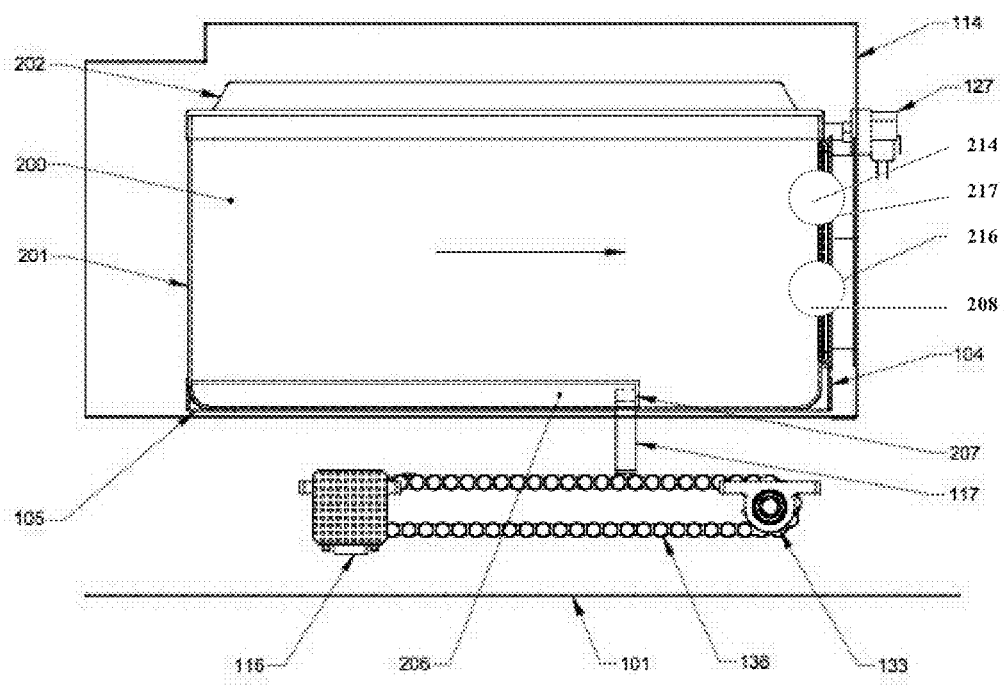
FIG. 4B is a cross-sectional side view depicting the instrument container fully inserted into the heating chamber.
Figure 5A:
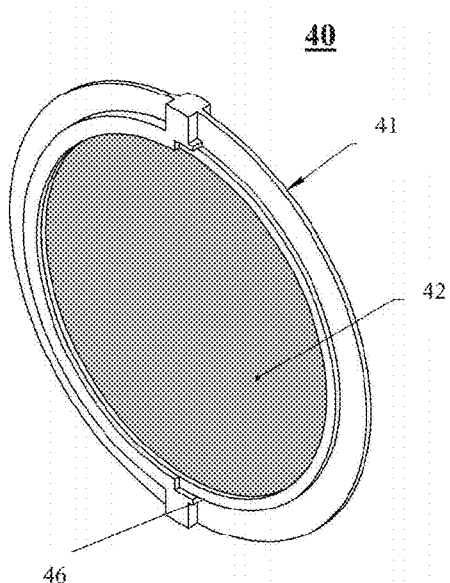
FIGS. 5A and 5B are perspective views of the butterfly valve depicting the valve in the closed and open positions, respectively.

Referring to FIGS. 3, 4A, and 4B, the high velocity hot air sterilizer 100 includes a sliding rack 104 and instrument container tray 105 which guides the instrument container 200 to the proper placement within the high velocity hot air sterilizer 100 for the engagement of the air supply portal 126 with the air supply valve plate 208 and the engagement of the air exhaust portal 118 with the air exhaust valve plate 214. The high velocity hot air sterilizer 100 includes a push bar 117 which is joined to a chain drive 136 which serves to ensure that the container 200 is fully inserted in the heating chamber 109. The container 200 includes a container guide slot 206 on the underside of the container. To assure that the instrument container 200 is fully inserted to the rear of heating chamber 109 and fully engaged with the air supply portal 126 (FIGS. 2 and 3) and air exhaust portal 118 (FIGS. 2 and 3) of the high velocity hot air sterilizer 100, the chain drive 136 with attached push bar 117 is engaged into and along the container guide slot 206 and driven by a stepper motor 116 which is activated by closing and the locking the door 103. FIG. 4A depicts the instrument container 200 partially inserted into the heating chamber 109 with the push bar 117 not yet engaged into the container guide slot 206. FIG. 4B depicts the instrument container 200 fully inserted into the heating chamber 109 with the push bar 117 fully engaged into and along the container guide slot 206. During insertion of the container 200 into the heating chamber 109, the push bar 117 is driven by the chain drive into the container guide slot 206 until the push bar 117 becomes engaged with the container guide slot terminal end 207, at which point the push bar 117 pushes the instrument container 200 to the rear of the heating chamber 109, this position is defined as the fully inserted position. With the instrument container 200 in the fully inserted position, the rear face of the instrument container 200 contacts a pressure switch 127, which is carried on the rear wall of the heating chamber wall 114. The pressure switch 127 turns off the stepper motor 116, locking the instrument container 200 in the fully inserted position. As shown in FIG. 2, vertical pressure rollers 137 are mounted on the upper interior surface of heating chamber wall 114 and provide guidance to assure that the instrument container 200 does not elevate during the transit to the fully inserted position. One or more valve posts 135 protrude from the interior rear heating chamber wall 114 (FIGS. 4A and 7). With the instrument container 200 in the fully inserted position, the valve posts 135 contact the air supply valve plate 208 (FIGS. 4B and 8) and the air exhaust valve plate 214 (FIG. 4B) of the instrument container 200 to fully open both the air supply valve plate 208 (FIGS. 4B, 6, and 8) and air exhaust valve plate 214 (FIGS. 4B and 6) to allow proper airflow to and from the instrument container 200. The air supply valve plate 208 and the air exhaust valve plate 214 are spring-loaded such that when the valve posts 135 do not contact the air supply valve plate 208 and the air exhaust valve plate 214, the air supply valve plate 208 and the air exhaust valve plate 214 revert to the closed and sealed position (FIG. 5A), thereby preventing air from entering the instrument container 200. With the door 103 in the closed position, the instrument container 200 is moved to and is held in the fully inserted position, thereby ensuring that when the door 103 is the closed position, the instrument container 200 is only capable of exchanging air with the air handling plenum 123. With the instrument container 200 in the fully inserted position, the air handling portal and the container portal are held in sealed contact, and are an opening through which air is exchanged between the instrument container 200 and the air handling plenum 123, further, the instrument storage chamber and the air handling plenum together define air-tight space which does not exchange air with the surroundings.

Figure 6:
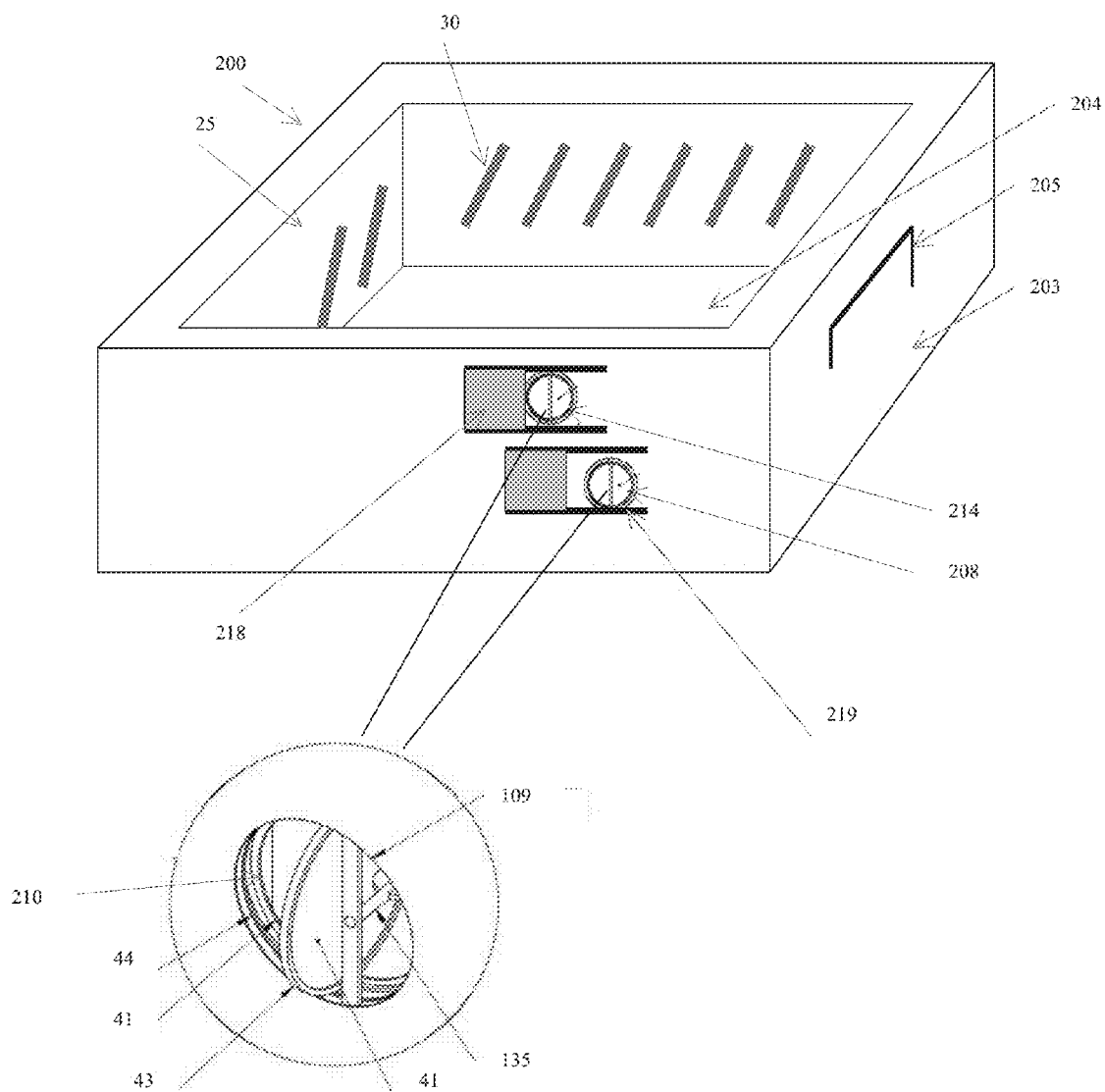
FIG. 6 is a perspective view of an instrument container with the lid removed with plenum insert and depicting the air supply and air exhaust valves in the open position.
Figure 7:
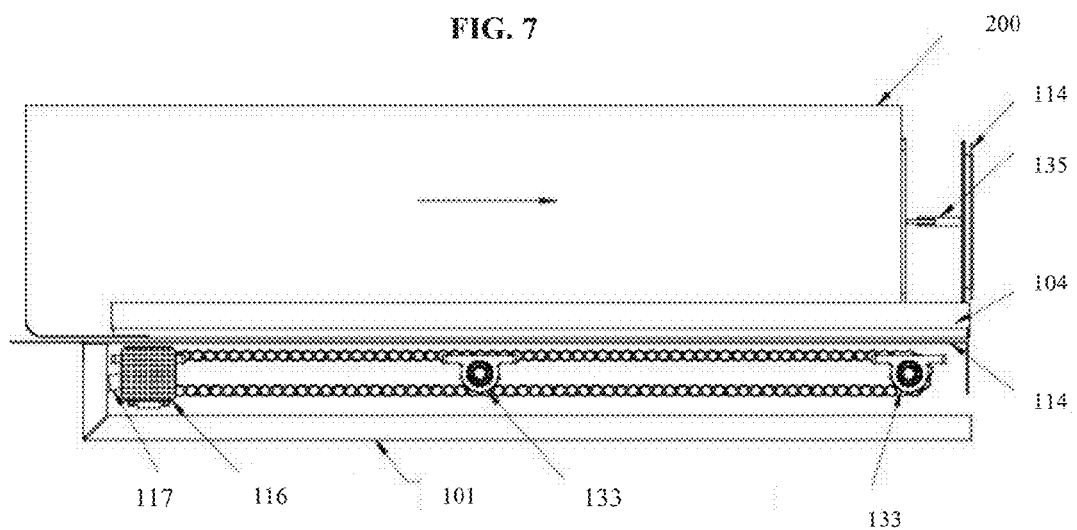
FIG. 7 is a cross-sectional side view depicting the instrument container partially inserted into the heating chamber showing closed air supply valve only.

Referring to FIGS. 4A and 6, the instrument container 200 is configured to accept and exhaust air provided from the high velocity hot air sterilizer 100 to sterilize medical and dental instruments, yet have the ability to prevent the influx of environmental microbial contaminants once the instrument container 200 is removed from heating chamber 109. The instrument container 200 has the basic elements of any typical container used in the sterilization of medical or dental instruments: the container includes a sealable latchable, microbial impervious lid 202; four sides 203, a bottom 204, and lifting handles 205 with all construction and components having the ability to withstand the rigor of physical use and materials, preferably aluminum, stainless steel or similar material capable of withstanding temperatures of 375° F. to 420° F., which temperature range is the preferred temperature range of the air during the sterilization cycles described herein. Together, the four sides 203 and the bottom 204 define a surrounding wall which defines an instrument storage chamber within the instrument container 200; the surrounding wall is solid and air-tight except for the air-supply access portal 216 and the air-exhaust access portal 217. Together, the air supply access portal 216 and the air exhaust access portal 217 serve as a container portal which allows air to enter and exit the instrument container 200; in the preferred embodiment, the container portal includes a pair of openings, though a single opening is envisioned. The surrounding wall also defines an open top (as shown in FIG. 6) through which instruments may be inserted in and removed from the instrument storage chamber. The lid 202 (as shown in FIGS. 4A and 4B) forms an air-tight seal with the surrounding wall to prevent air from entering of leaving the instrument container 200 through the open top when the lid is in place. The lid 202 is removably and sealably mounted to the instrument container 200 to cover and seal the open top. With the lid in place, air is only able to enter and exit the instrument container 200 through the container portal—air is unable to pass through the surrounding wall, the lid 202, or the interface between the lid 202 and the surrounding wall. The vertical pressure rollers 137 preferably contact the lid 202, as shown in FIG. 2, and serve to hold the container 200 in a preferred orientation within the high velocity hot air sterilizer 100.

For successful sterilization of medical and dental instruments by high velocity hot air, it is necessary that the instrument container 200 receives supplied hot air at a high velocity, preferably 1500 to 3000 feet per minute, without the encumbrances of filters or other devices that reduce air velocity. Referring to FIGS. 4B and 6, an air supply valve plate 208 and an air exhaust valve plate 214 are viewed in the open position allowing direct, unencumbered high velocity hot air to enter the instrument container 200 via the air supply access portal 216 and exit the instrument container 200 via the air exhaust access portal 217. No filters are used with the instrument container 200 or the high velocity hot air sterilizer 100. Filters are unnecessary since the air is segregated within the instrument container 200 and the air handling system.

Figure 8:
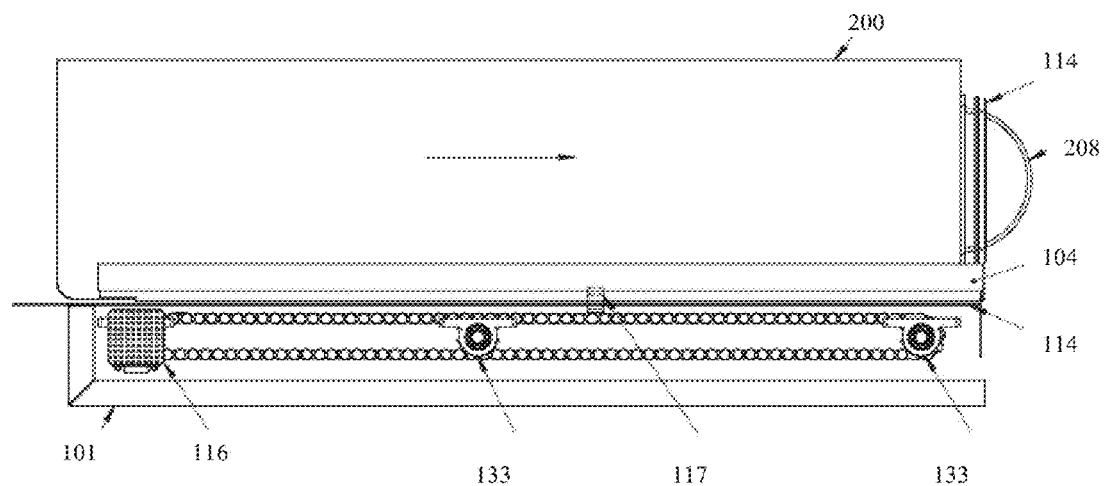
FIG. 8 is a cross-sectional side view depicting the instrument container fully inserted into the heating chamber showing open air supply valve only.

Referring to FIGS. 3, 4B and 8, with the instrument container 200 in the fully inserted position, the fixed posts 135 extend from the heating chamber wall 114 and protrude through the air supply access portal 216 and air exhaust access portal 217 to contact and push the air supply valve plate 208 and the air exhaust valve plate 214 to the open position.

Referring to FIG. 3, a first air portal gasket 134 circumscribes the air supply portal 126 providing a sealed perimeter between the air supply portal 126 and the air exhaust access portal 217. A second air portal gasket 134 circumscribes the air exhaust portal 118 providing a sealed perimeter between the air exhaust portal 118 and the air supply access portal 216. Each of the portal gaskets 134 nests within respective portal gasket contours 215 which surround the respective air supply access portal 216 and air exhaust access portal 217.

Figure 10:
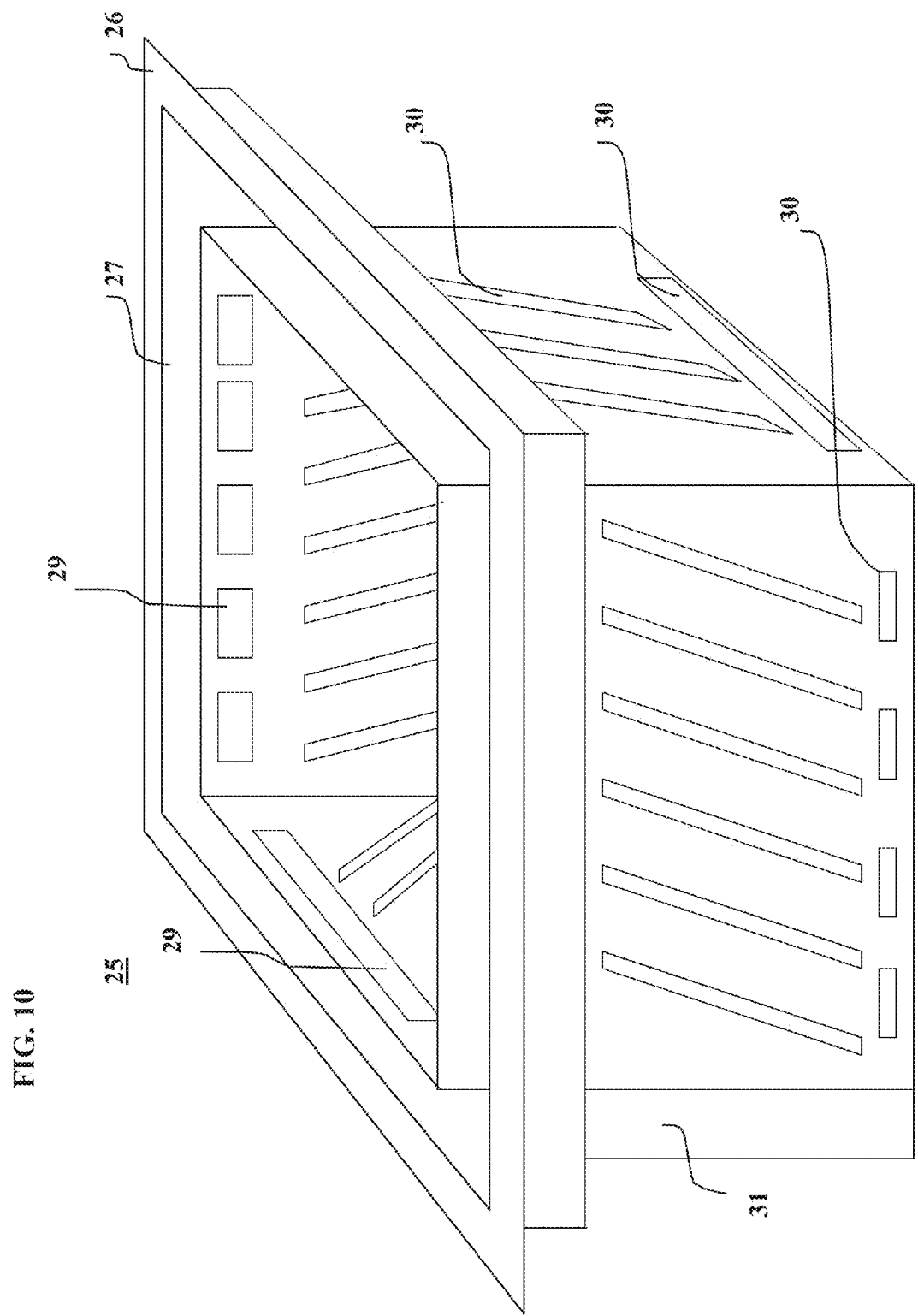
FIG. 10 is a perspective view of the instrument container's plenum insert.
Figure 12:
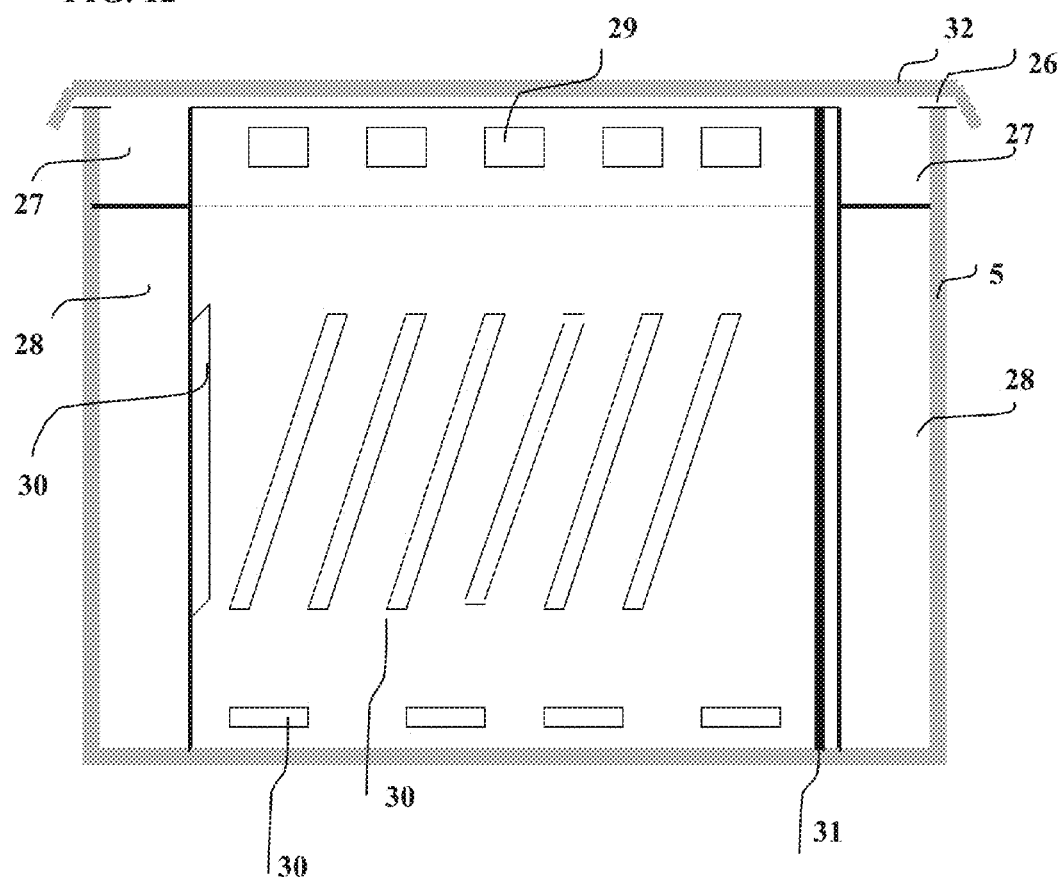
FIG. 12 is a front sectional elevation view of the plenum insert within the instrument container.

Referring to FIGS. 4B, 8, and 7, with the air supply valve plate 208 in the open position, high velocity hot air enters the instrument container 200 only from the air handling plenum 123 during the sterilization cycle. FIG. 10 depicts the plenum insert 25 which is placed into the instrument container 200, positioned to direct the hot, high velocity air through the interior air supply plenum 28 and to exhaust air through the interior air exhaust plenum 27. The interior air supply plenum 28 completely encircles the bottom three-quarters of the instrument container 200, having as interior wall of the instrument container 200 as its exterior wall and the exterior wall of the plenum insert 25 as its interior wall. The bottom of the instrument container 200 serves as the bottom of the interior air supply plenum 28 and exterior bottom of the interior exhaust plenum 27 serves as the top of the interior air supply plenum 28. The interior exhaust plenum 27 encircles the top one-quarter of the instrument container 200 with the interior of the container lid 202 serving as the top of the interior exhaust plenum 27. The container lid 32 and plenum cover flange 26 are mated with opposing gaskets to form a tight seal when the container lid 32 is securely latched into place (FIG. 12).

Figure 11A:
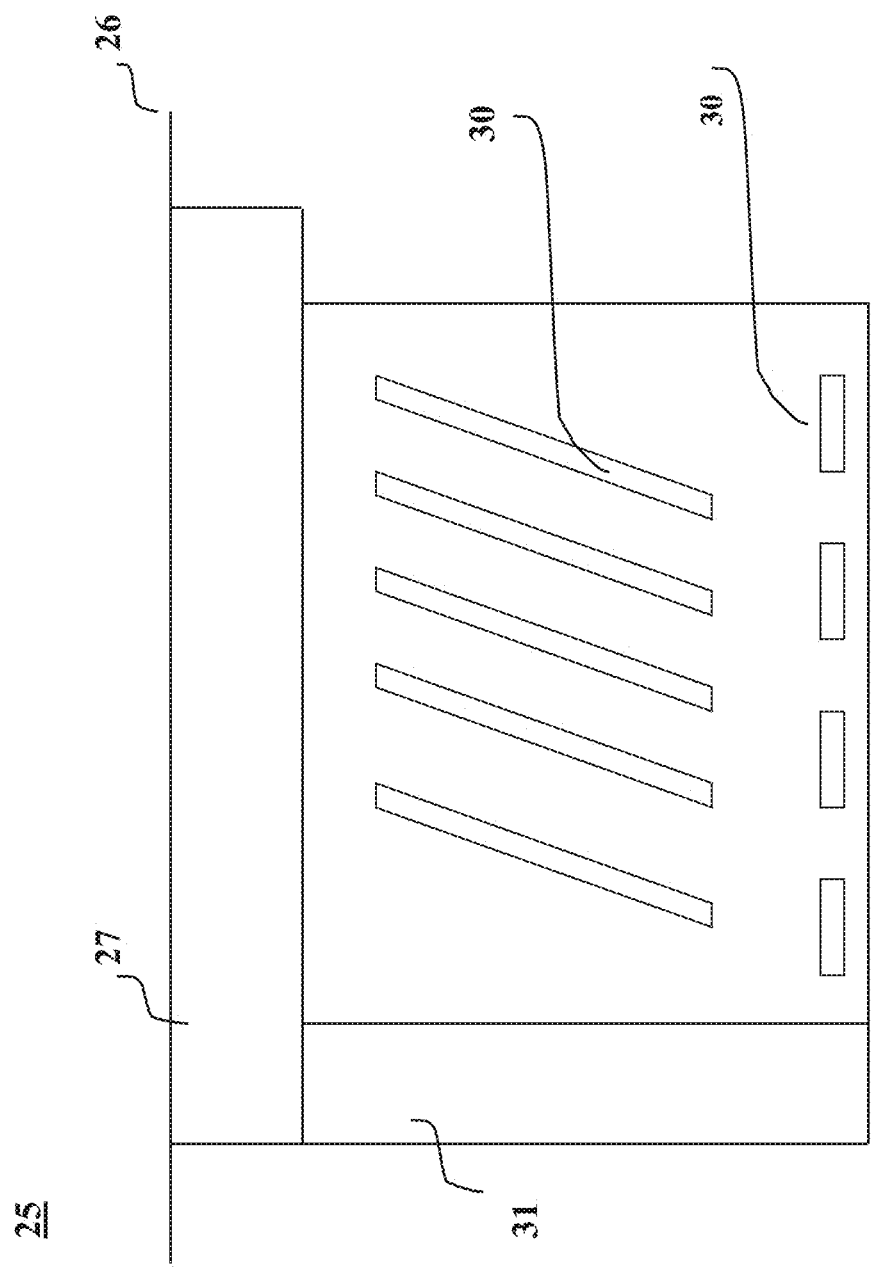
FIG. 11A is a side elevation view of the instrument container's plenum insert.

Hot, high velocity airflow into the instrument container 200 is forced unidirectionally around the interior of the plenum insert 25 by means of a supply air plenum flange 31. FIGS. 11A and 11B are side and front elevation views, respectively, of the plenum insert 25, depicting the side view and front view of the supply air plenum flange 31. As the air moves directional air supply vents 30 force the air into the interior of the plenum insert 25 that contains the instruments to be sterilized. The directional air supply vents 30 are slanted and fluted (FIG. 10) to move the air in a circular and upward motion within the instrument container's 200 interior to provide uniformity of air distribution. Generating a slight negative air pressure to the interior exhaust plenum 27 by means of the circulating fan 115 (FIG. 2) pulls air at the top of the interior of plenum insert 25 through the air exhaust vents 29 and redirects the exhaust air back to the air exhaust portal 118 where the spent air is discharged to the air handling system of the high velocity hot air sterilizer 100 to re-heat the air with the electric heating element 132 and to increase the velocity of the air for recirculation with the fan 115.

Upon completion of the sterilization cycle and before the door 103 is opened, the instrument container 200 is separated from the back heating chamber wall 114 by the automatic reversal of the stepper motor 116, moving the chain drive with attached push bar 117 to the front of the high velocity hot air sterilizer 100, relieving the pressure exerted to the rear of the heating chamber 109 and allowing the spring-loaded air supply valve plate 208 and the air exhaust valve plate 214 to revert back to the closed position and uncoupling the instrument container 200 from the air supply portal 126 and air exhaust portal 118 and extracting the fixed posts 135 from the air supply access portal 216 and air exhaust access portal 217.

Figure 5B:
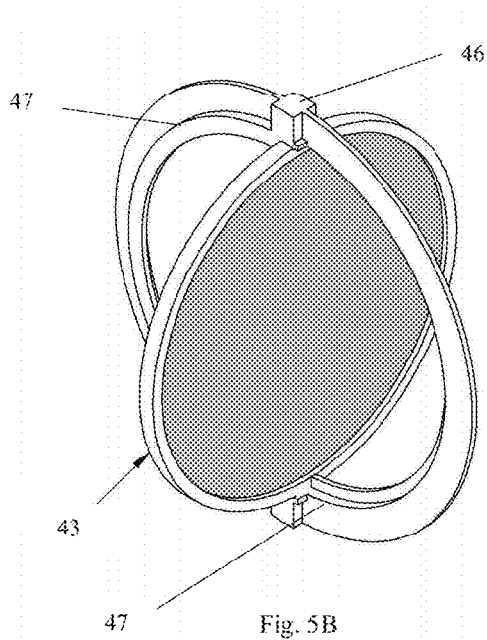
Figures 9A, 9B:
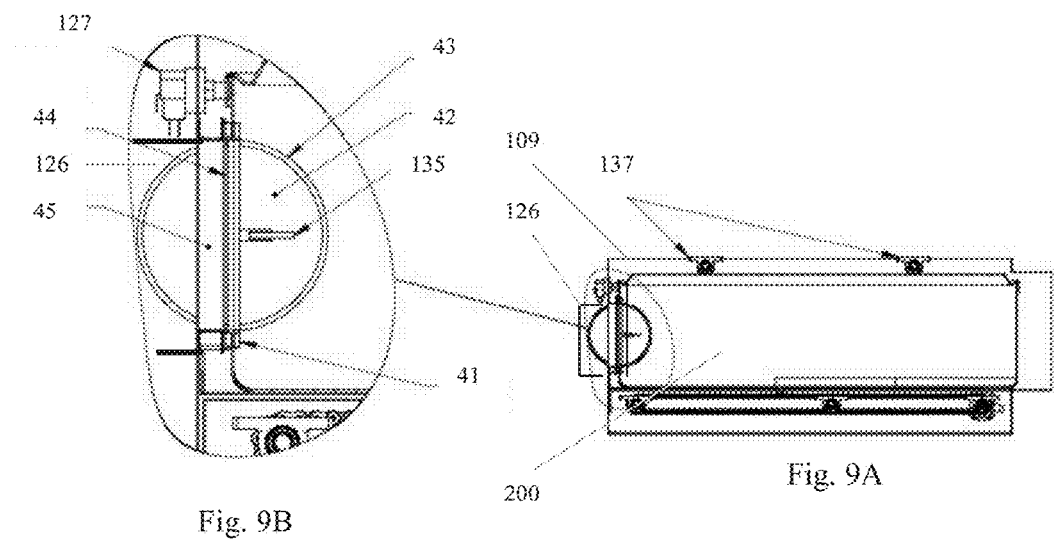
FIG. 9 is a cross-sectional side view of an instrument container's air supply valve plate in the open configuration.

Referring to FIGS. 5 and 9, the valve assembly 40 consists of a circular valve plate 42 encompassed by a valve frame 41. The circular valve plate 42 pivots unidirectionally, perpendicular to and within the circular valve frame 41 by means of two compression spring spindles 46 placed 180 degrees apart. The valve frame 41 has two hemispheric groves 47, located on opposite sides of the valve frame 41 that allow the valve plate to set flush in the closed position. The valve plate 42 is sealed along the outer circumference of the valve plate against the inner circumference of the valve frame 41 by means of molded valve gasket 43. The valve assembly 40 is mounted and sealed in the instrument container wall 201. During the sterilization cycle the chamber wall gasket 44 mounted within a gasket collar 45 seals the juncture of the valve assembly against the rear chamber wall 114 to provide a sealed and air-tight perimeter when in the closed configuration.

Referring to FIG. 6, access portal protective covers 218 provide protection to the air supply access portal 216, the air supply valve plate 208, the air exhaust access portal 217, and the air exhaust valve plate 214 from accidental damage or intrusion and act as a secondary barrier to environmental microbial contaminants. The access portal protective covers 218 are movable along protective cover rails 219. Following removal of the instrument container 200 upon completion of the sterilization cycle from the heating chamber 109, the access portal protective covers 218 are manually moved across the air supply access portal 216 and air exhaust access portal 217 by sliding the access portal protective covers 218 along the protective cover rails 219. In an alternative embodiment, the access portal protective covers 218 are opened and closed by mechanical action during insertion and removal of the instrument container 200.

Referring to FIGS. 2 and 3, hot air is generated and circulated to and through the instrument container 200 by the air handling system, which consists of a circulating fan 115, an electric heating element 132, and an air handling plenum 123. The circulating fan 115 brings the air to a velocity necessary to achieve rapid sterilization as monitored by an air flow monitor 130 located in the air handling plenum 123 just downstream from the from the circulating fan 115 and the electric heating element 132 near the entrance to the air supply portal 126. Air is blown over the electric heating element 132 to raise the temperature of the air to the desired temperature necessary for microbial kill at the required sterilization times. The electric heating element 132 is thermostatically controlled by two thermocouple monitors, an air supply thermocouple 128 and an air exhaust thermocouple 129, to maintain the air within the heating chamber 109 within a desired temperature range. The air supply thermocouple 128 is located within the air supply portal 126 to monitor the temperature of the air as the air is directly supplied to the instrument container 200. Air discharged from the instrument container 200 is monitored by the air exhaust thermocouple 125 located at the air exhaust portal 118. To ensure the sterilization cycle initiates with air in the instrument container 200 at the proper sterilization temperature, both the air exhaust thermocouple 128 and air supply thermocouple 129 must be at the desired temperature to achieve sterilization before the sterilization cycle is activated.

Heated high velocity air circulates from the air handling plenum 123 which directs the air into the instrument container 200 via the air supply portal 126 and the open air supply valve plate 208 (FIG. 3) for uniform distribution throughout the instrument container 200 as assisted by an internal air diversion insert plenum 25. As hot high velocity air is supplied to the instrument container 200, a portion of the air is returned to the circulating fan 115 and electric heating element 132 by way of the open air exhaust valve plate 214 and the air exhaust portal 118. This continuous process continues throughout the sterilization cycle, keeping the sterilant air at its designated temperature and velocity during the whole of the sterilization cycle without influx of any outside microbiological contaminants to jeopardize the sterilization process. The air handling system remains closed and sealed, creating a slightly positive air pressure to preclude the influx of air into the air handling system if a seal were to fail. The slight positive air pressure differential is monitored with an air pressure monitor 131 located at the entrance of the air supply portal 126 to ensure the air handling system retains a positive pressure. If the air pressure becomes negative, this negative pressure will be measured by the air pressure monitor 131, and the air pressure monitor 131 will provide an electronic signal which will be used to terminate the sterilization cycle. As apparent to those skilled in the art, the air handling system can also be designed to deliver and exhaust air not only from the sides of the instrument container 200, but also from the top and bottom, separately or in conjunction to assure airflow requirements and heat distribution necessary to sterilize the contained instruments.

It is understood that while certain aspects of the disclosed subject matter have been shown and described, the disclosed subject matter is not limited thereto and encompasses various other embodiments and aspects. No specific limitation with respect to the specific embodiments disclosed herein is intended or should be inferred. Modifications may be made to the disclosed subject matter as set forth in the following claims.

What is claimed is:

1. A plenum insert, comprising:
   an internal wall defining an instrument storage area with an internal top opening;
   an air supply plenum flange protruding from a side of said internal wall;
   air supply vents opening at intervals across said internal wall;
   air exhaust vents opening at intervals across an upper end of the internal wall; and
   an exhaust plenum, comprising:
      an upper wall defining an upper top opening larger than said internal top opening;
      an upper floor connecting said upper wall to said interior wall; and
      a plenum cover flange circumscribing said upper top opening.

2. The plenum insert of claim 1, wherein said instrument storage area does not have a bottom.

3. The plenum insert of claim 1, wherein said air supply plenum flange protrudes outward from a corner of said internal wall and has substantially the same height as said internal wall.

4. The plenum insert of claim 1, wherein said upper floor connects to said interior wall below said air exhaust vents, and the top of said internal wall and the top of said upper wall are approximately equal in height.

5. The plenum insert of claim 1, wherein the outermost extremity of said air supply plenum flange reaches a side of said upper wall.

6. The plenum insert of claim 1, wherein a gasket is attached to said plenum cover flange.

\* \* \* \* \*